United States Patent

Chaudhuri et al.

[11] Patent Number: 4,886,890
[45] Date of Patent: Dec. 12, 1989

[54] DIQUARTERNARY NITROGEN COMPOUNDS

[75] Inventors: Ratan K. Chaudhuri, Butler; David J. Tracy, Lincoln Park; Robert B. Login, Oakland, all of N.J.

[73] Assignee: GAF Corporation, Wayne, N.J.

[21] Appl. No.: 250,587

[22] Filed: Sep. 29, 1988

[51] Int. Cl.⁴ ............................................. C07D 207/00
[52] U.S. Cl. ..................................... 548/519; 546/188; 540/362; 540/524; 540/525; 540/1; 514/422
[58] Field of Search ................... 260/501.15; 548/519; 546/188; 540/362, 524, 525, 1

[56] References Cited

U.S. PATENT DOCUMENTS 2,933,529  4/1960  Hua ................................ 260/501.15
4,174,443 11/1979  Dalton ................................ 548/228

OTHER PUBLICATIONS

CA 106:101731b *Belyaev*, 1986.
CA 81:115553x *Seydel*, 1973.

*Primary Examiner*—Mukund J. Shah
*Assistant Examiner*—Frederick F. Tsung
*Attorney, Agent, or Firm*—Marilyn J. Maue; Joshua J. Ward

[57] ABSTRACT

This invention relates to quaternary compounds having the formula

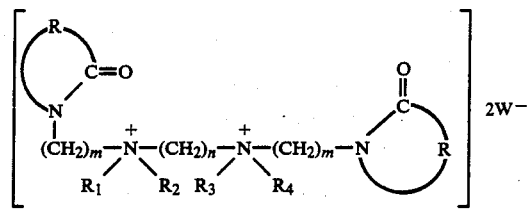

wherein $W^-$ is an anion; m and n are integers having a value of from 1 to 4; R is alkylene having from 3 to 8 carbon atoms; $R_1$ is a radical having from 8 to 25 carbon atoms and is selected from the group of alkyl, alkenyl and alkoxy alkylene and each of $R_2$, $R_3$ and $R_4$ is a radical having from 1 to 25 carbon atoms and is alkyl, alkoxy or

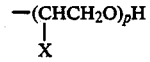

where p has a value of from 1 to 4 and X is hydrogen or methyl. The invention also relates to the preparation and use of said diquaternized compounds.

6 Claims, No Drawings

DIQUARTERNARY NITROGEN COMPOUNDS

In one aspect the invention relates to novel quaternized compounds which possess anti-microbal properties, high complexing ability and conditioning properties for hair and skin, particularly when forumlated with anionic surfactants.

BACKGROUND OF THE INVENTION

The selection of components for hair and skin treating formulations presents numerous difficulties involving compatibility. Several hair treatment and shampoo formulations have been developed which aim to provide conditioning action during cleansing so as to leave the hair soft, manageable and lustrous and thus to eliminate a separate application of creme rinses or conditioning treatments. Such shampoo formulations have employed conventional anionic surfactants such as sodium lauryl sulfate, ammonium lauryl sulfate, and sodium lauryl ether sulfate as major components. Problems arise from the limited compatability of anionic detergents with commercial cationic conditioning agents which precipitate out of solution in shampoo formulations.

Still another problem encountered in hair conditioning shampoos is one of a perservative nature. It has been found that shampoos, containing inadequate preservative, on standing develop strands of pseudomonas aerouginosa which are clearly visible in the liuqid and which may cause scalp infection. Consequently, separate biocidal agents are needed to prevent development of this bacteria and prevent skin infection. These and many other problems are encountered in the formulation of various shampoos, conditioners and cream rinses. Certain of these difficulties are also encountered in skin lotions, healing salves, mouthwashes, etc.

Accordingly it is an object of this invention to minimize or obviate the above problems while providing additional benefits in hair and skin treating formulations.

Another object of the invention is to provide novel quaternized nitrogen containing compounds having increased complexability and other unique properties.

Another object is to provide novel quaternized nitrogen containing compounds having excellent hair conditioning as well as anti-microbal properties when incorporated into a shampoo and having high compatibility with components of hair and skin treating formulations.

Another object is to provide an economical and commercially feasible method for the preparation of said novel quaternized nitrogen containing compounds.

Still another object is to provide processes for the use of said quaternized compounds.

These and other objects will become apparent from the following description and disclosure.

THE INVENTION

According to this invention there is provided a diquaternized compound having unique properties and defined by the formula

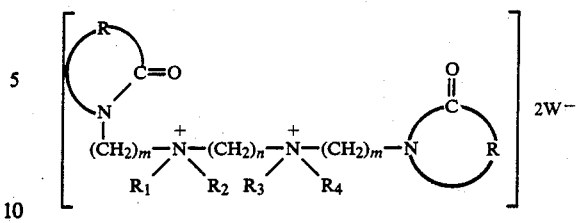

wherein $W^-$ is a chloride, bromide, iodide, p-tosylate or a lower alkyl sulfate anion; m and n are integers having a value of from 1 to 4; R is alkylene having from 3 to 8 carbon atoms; $R_1$ is a radical having from 8 to 25 carbon atoms and is selected from the group of alkyl, alkenyl and alkoxy alkylene; and each of $R_2$, $R_3$ and $R_4$ is a radical having from 1 to 25 carbon atoms and is alkyl, alkoxy or

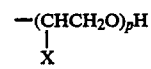

where p has a value of from 1 to 4 and X is hydrogen or methyl. Preferred compounds are those wherein at least one of $R_2$, $R_3$ and $R_4$ is lower alkyl.

The most preferred compounds embraced by the above formula are those wherein $R_1$ is a radical having from 8 to 18 carbon atoms and is alkyl or alkoxy alkylene; $R_2$, $R_3$ and $R_4$ are each lower alkyl and m has a value of 1.

Examples of diquaternized compounds within the preferred group include

N,N,N'-trimethyl-N'-nonyl bis(pyrrolidonylmethyl)-1,2-ethylene diammonium salt

N,N,N'-trimethyl-N'-octadecyl bis(pyrrolidonylmethyl)1,2-ethylene diammonium salt N,N,N'-triethyl-N'-tetradecyl bis(pyrrolidonylmethyl)-1,3-propylene diammonium salt N,N,N'-trimethyl-N'-octadecyl bis(pyrrolidonylmethyl)-1,4-butylene diammonium salt N,N,N'-triethyl-N'-dodecyloxyethylene bis(pyrrolidonylmethyl)-1,2-ethylene diammonium salt N,N,N'-tripropyl-N'-tetradecenyl bis(pyrrolidonylmethyl)-1,2-ethylene diammonium salt N,N-dimethyl-N',N'-dioctadecyl bis(pyrrolidonylmethyl)-1,2-ethylene diammonium salt N,N,N'-tridodecyl-N'-methyl bis(pyrrolidonylmethyl)-1,2-ethylene diammonium salt N,N,N'-trimethyl-N'-nonyl bis(pyrrolidonylethyl)-1,2-ethylene diammonium salt The present quaternary compounds possess unique properties, among which is their high complexability provided by the multiple lactam sites in the compound. Accordingly, the present compounds can be employed to solubilize water insoluble substances such as drugs, skin and hair emollients, etc. These compounds are particularly recommended for cosmetic applications since they provide high conditioning together with anti-microbal properties which extend the shelf life of the cosmetic products. The present compounds are highly compatible with alpha-olefin sulfonates and anionic surfactant salts which are conventionally employed in shampoos and skin lotions. Cosmetic uses for the compounds of this invention include mouthwashes, lotions to control bacterial infections of the skin, moisturizing lotions, hair conditioners, and many other cosmetic uses. In addition, these compounds can be formulated in laundry detergents and rinsing aids to provide fabric softening and antistatic properties. Generally, when employed for any of the above uses, between about 0.05% and about 25% by weight, preferably between about 0.5 and about 15% by weight of the diquaternary compound is added to an existing formulation.

The diquaternary compounds of this invention are prepared by an economically feasible and commercially practicable process which involves the reaction between a tertiary diamine and an N-haloalkyl lactam having a 5 to 10 membered ring. A general method for the preparation is defined by the addition reaction:

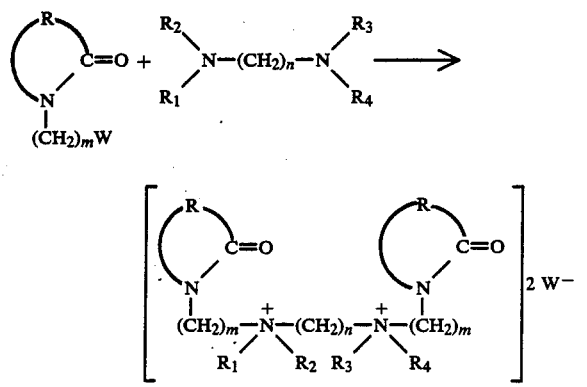

In the above reaction, the mole ratio of ditertiary amine to lactam should be maintained close to stoichiometry as indicated, i.e. a ratio of about 2:1. Although ratios of 1:1 to about 2.5:1 can be employed, some sacrifice to the yield of desired product results. Also reaction mixtures are formed from which the reaction product is difficult to separate.

Preferred tertiary diamines employed in the present process are those wherein $R_2$, $R_3$ and $R_4$ are lower alkyl and $R_1$ is an alkyl or alkoxy lower alkylene radical having from 8 to 18 carbon atoms, for example, N,N,N'-trimethyl-N'-nonyl-1,2-ethylenediamine
N,N,N'-trimethyl-N'-octadecyl-1,2-ethylenediamine
N,N,N'-triethyl-N'-tetradecyl-1,3-propanediamine
N,N,N'-trimethyl-N'-octadecyl-1,4-butanediamine
N,N,N'-triethyl-N'-dodecyloxyethylene-1,2-ethylenediamine
N,N-dimethyl-N',N'-dioctyl-1,2-ethylenediamine
N,N,N'-triethyl-N'-dodecenyl-1,2-ethylenediamine.

Examples of other tertiary diamines include
N,N-dimethyl-N'-ethyl-N'-octyl-1,3-propanediamine
N,N-dioctyl-N',N'-dimethyl-1,4-butanediamine
N,N-diethyl-N',N'-dioctadecyl-1,2-ethylenediamine
N,N,N'-trioctyl-N'-methyl-1,4-butanediamine
N,N-dipropyl-N'-methyl-N'-dodecenyl-1,3-propanediamine
N,N-dimethyl-N',N'-dioctadecenyl-1,3-propanediamine
N,N,N',N'-tetraoctyl-1,2-ethylenediamine
N,N'-dimethyl-3,6-dioxa-9,12-diaza-tetraeicosae-1-ol
N,N'-diethyl-3-oxa-6,9-diaza-heptadecane-1-ol.

Examples of suitable lactam reactants include the N-chloromethyl, N-bromomethyl and N-iodomethyl derivatives of 2-pyrrolidone, 4-methyl-2-pyrrolidone, 4-butyl-2-pyrrolidone, 2-piperidone, 3-methyl-2-piperidinone, 2-caprolactam, hexahydro-2-(1H)-azacinone, octahydro-2-(1H)-azacinone and $C_1$ and $C_4$ alkyl substituted derivatives located on an alkylene group in the heterocyclic ring of these lactams. Mixtures of these lactam reactants can also be employed to provide a correspondingly mixed quaternary product, if desired. Of these lactam reactants the N-halomethyl-2-pyrrolidones and N-halomethyl caprolactams are preferred and the N-chloromethyl lactams are most preferred.

The reaction is carried out by contacting the ditertiary amine and the halolactam at a temperature between about 20° C. and about 65° C. preferably between about 40° C. and about 55° C. under a pressure of from about 0 to about 40 psig, preferably atmospheric pressure for a period of from about 5 minutes to 5 hours, more desirably from about 10 to about 30 minutes.

Although the reaction may be carried out in the absence of a solvent, dilution of the reactants with a suitable anhydrous solvent is desirable for better control of the exothermic reaction. Such suitable solvents include ketones, for example acetone, and methylethyl ketone, hydrocarbons such as hexane, and heptane, esters for example ethyl acetate and ethers for example tetrahydrofuran. Such solvents, when employed, generally comprise between 20 and 80%, preferably 25 to 30%, of the reaction mixture.

It is also recommended that the haloalkyl lactam reactant be added gradually, dropwise or intermittently to the ditertiary amine. Upon completion of the reaction, a solid product is formed and recovered. Since the reaction is quantitative, the product can be used as is or, when a slight excess of the diamine is employed, it can be neuturalized, if desired, with an acid such as hydrochloric acid, acetic acid, lactic acid or citric acid.

For incorporating into a standard formulation of shampoo, cream rinse, hand or body lotion, etc., the present product is dissolved in an inert solvent such as water, propylene glycol, ethanol, etc., and the solution in the desired amount is mixed into the formulation to provide a homogeneous liquid, gel, cream or lotion. Incorporation of the present product is usually affected at room temperature under atmospheric pressure and requires no special formulating technique. However, for certain formulations, incorporation of the present product can be effected at temperatures up to about 85° C. Amphoteric-containing shampoo formulations are best prepared by initially forming an aqueous solution of the quaternized product and the amphoteric surfactant and then adding the solution to the shampoo formulation.

Having generally described the invention, reference is now had to the accompanying examples which set forth preferred embodiments, but which are not to be construed as limiting to the scope of the invention as more broadly set forth above and in the appended claims.

EXAMPLE 1

To a 1 liter, 4-neck flask equipped with mechanical stirrer, reflux condenser, thermometer, and dropping funnel was added N,N,N'-trimethyl-N'-octadecyl-1,3-propanediamine (1.02 mole) which was heated with stirring to 40° C. under $N_2$ blanket after which the heating source was removed and N-chloromethyl-2-pyrrolidone (2 mole) was added to the amine dropwise over a period of 20 minutes. An exothermic reaction ensued and was controlled between 45°–55° C., by the rate of addition of N-chloromethyl-2-pyrrolidone. The reaction mixture became viscous during the addition of N-chloromethyl-2-pyrrolidone and remained as viscous liquid on completion of the reaction. The yield of N,N,N'-trimethyl-N'-octadecyl-N,N'-bis[(2-pyrrolidonyl)-methyl]-1,3-propane diammonium chloride was almost quantitative. The content of the quaternary compound was determined by titration. (Mercuric Acetate method as described by Sidney Siggia, "Quantitative Analysis via Functional Group", 1963, 3d Ed., John Willey & Sons, pgs 552–554).

EXAMPLE 2

The reaction of Example 1 was repeated except that the amine used was N,N,N'-trimethyl-N'-dodecyl-1,2-ethanediamine (bp. 130°–135° C. at 1 mm Hg). The corresponding N,N,N'-trimethyl-N'-dodecyl-N,N'-bis[(2-pyrrolidonyl)methyl]-1,2-ethane diammonium chloride was obtained in quantitative yield.

EXAMPLE 3

The reaction of Example 1 was repeated except that the amine used was N,N,N'-trimethyl-N'-nonyl-1,2-ethanediamine (bp. 135°–139° C. at 1 mm Hg). The corresponding N,N,N'-trimethyl,N'-nonyl-N,N'-bis[(2-pyrrolidonyl)methyl]-1,2-ethane diammonium chloride was obtained in quantitative yield.

EXAMPLE 4

The reaction of Example 1 was repeated except that the amine used was N,N,N'-trimethyl-N'-[3-(octadecyloxy)propyl]-1,3-propanediamine. The corresponding N,N,N'-trimethyl,N'-[3-(octadecyloxy)propyl]-1,3-propanediamine. The corresponding N,N,N'-trimethyl,N'-[3-(octadecyloxy)propyl]-N,N'-bis[(2-pyrrolidonyl)methyl]-1,3-propane diammonium chloride was obtained in quantitative yield.

EXAMPLE 5

The reaction of Example 1 was repeated except that the amine used was N,N,N'-trimethyl-N'-[3-(tetradecyloxy)propyl]-1,3-propanediamine. The corresponding N,N,N'-trimethyl-N'-[3-(tetradecyloxy)propyl]-N,N'-bis[(2-pyrrolidonyl)methyl]-1,3-propane diammonium chloride.

EXAMPLE 6

The reaction of Example 1 was repeated except that the alkylating agent used was N-chloromethyl-2-azacycloheptanone. The corresponding N,N,N'-trimethyl-N'-octadecyl-N,N'-bis-[(2-azacycloheptanoyl)methyl]-1,3-propane diammonium chloride was obtained in quantitative yield.

EXAMPLE 7

The reaction of Example 1 was repeated except that the amine and alkylating agent used were N,N,N'-trimethyl-N'-[2-(tridecyloxy)ethyl]-1,3-propanediamine and N-chloroethyl pyrrolidone. The corresponding N,N,N'-trimethyl-N'-[2-(tridecyloxy)ethyl], N,N'-bis[2-(2-pyrrolidonyl)ethyl]-1,3-propane diammonium chloride was obtained in almost quantitative yield.

EXAMPLE 8

The reaction of Example 1 was repeated except that the amine was dissolved in about 1 liter of anhydrous acetone. The resulting diquaternized product was isolated by filtration with a yield of about 94% and a purity of 98%.

EXAMPLE 9

A cream hair rinse was prepared by mixing in a 1 liter beaker the following components at 50° C.

| Ingredients | Parts by Wt. |
| --- | --- |
| cetyl alcohol | 2.0 |
| emulsifying wax | 2.0 |
| citric acid | to pH 4 |
| deionized water | 93.7 |
| jasmine fragrance | 0.2 |
| preservative Kathon CG* | 0.1 |

To this mixture was added 2 parts by weight of N,N,N'-trimethyl-N'-octadecyl-N,N'-bis[(2-pyrrolidonyl) methyl]-1,2-ethane diammonium chloride.

EXAMPLE 10

The above procedure of mixing ingredients in water was repeated except that the following ingredients were substituted to produce a conditioning shampoo.

| Ingredients | Parts by Wt. |
| --- | --- |
| polyquaternium 11 | 0.5 |
| sodium laureth-4-phosphate | 0.8 |
| ammonium lauryl sulfate | 40.0 |
| silk protein | 0.25 |
| tetrasodium ethylenediamine tetra-acetic acid | 0.2 |
| deionized water | 58.05 |
| jasmine fragrance | 0.2 |

*a mixture of 5-chloro-2-methyl-4-isothiazolin-3-one and 2-methyl-4-isothiazolin-3-one To this aqueous mixture was added 2 parts by weight of N,N,N'-trimethyl-N'-octadecyl-N,N'-bis[(2-pyrrolidonyl)methyl]-1,2-propane diammonium chloride.

EXAMPLE 11

The procedure of Example 9 was repeated except that the following ingredients were substituted to produce a liquid hair conditioner.

| Ingredients | Parts by Wt. |
| --- | --- |
| PEG-8 Distearate | 2.5 |
| mineral oil | 1.5 |
| lanolin alcohol | 1.0 |
| stearic acid | 1.0 |
| PPG-20 methyl glucose ether | 1.0 |
| hydrolized animal protein | 0.25 |
| citric acid | to pH 4 |
| deionized water | 92.45 |
| preservative Kathon CG | 0.1 |
| lavender fragrance | 0.2 |

To this aqueous mixture was added 4 parts by weight of N,N,N'-trimethyl-N'-octadecyl-N,N'-bis[(2-azacycloheptanoyl)methyl]-1,2-ethane diammonium chloride.

Application of the formulations of Examples 9–11 left the hair unusually soft and silky. The preparations of Examples 9–11 also displayed good shelf life with no precipitation or clouding for an extended period of time.

EXAMPLE 12

The general procedure followed in Example 9 was repeated except that the following ingredients were substituted to prepare a liquid fabric softener which can be added to laundery or rinse water.

| Ingredients | Parts by Wt. |
| --- | --- |
| Miranol DM (sodium salt of stearic acid) | 3.00 |
| lavender fragrance | 0.25 |
| H$_2$O | 96.75 |

To this aqueous mixture was added 2 parts by weight of N,N-dimethyl-N,N'-dioctadecyl-N,N'-bis [(2-pyrrolidonyl)methyl]-1,3-propane diammonium chloride.

EXAMPLE 13

The general procedure of Example 9 was repeated except that the following ingredients were substituted to prepare a liquid fabric softener and anti-static agent which could be added to laundry or rinse water.

| Ingredients | Parts by Wt. |
| --- | --- |
| Igepal CO-660** | 23.0 |
| Ethanol | 15.0 |
| lavender fragrance | 0.9 |
| H$_2$O | 61.1 |

**100% active liquid/liquid condensation product of nonyl alcohol and ten units of ethylene oxide.

To this aqueous mixture was added 5.4 parts by weight of N,N-dimethyl-N,N'-dioctadecyl-N,N'-bis[(2-pyrrolidonyl)methyl]-1,3-propane diammonium chloride.

The formulations of Examples 12 and 13 showed superior softening of fabrics and increased fluffiness for napped fabrics. In addition, excellent anti-static properties were imparted by the formulation of Example 13.

What is claimed is:

1. The diquaternized compound having the formula

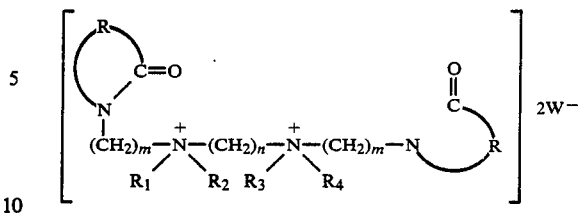

wherein $W^-$ is an anion; m and n are integers having a value from 1 to 4; R is alkylene having from 3 to 8 carbon atoms; $R_1$ is a radical having from 8 to 25 carbon atoms and is selected from the group of alkyl, alkenyl and alkoxy alkylene and each of $R_2$, $R_3$ and $R_4$ is a radical having from 1 to 25 carbon atoms and is alkyl, alkoxy or

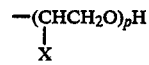

where p has a value of from 1 to 4 and X is hydrogen or methyl.

2. The diquaternized compound of claim 1 wherein $R_1$ is a radical having from 8 to 18 carbon atoms and is alkyl or alkoxy alkylene; at least one of $R_2$, $R_3$ and $R_4$ is lower alkyl and m has a value of 1.

3. The diquaternized compound of claim 2 wherein each of $R_2$, $R_3$ and $R_4$ is lower alkyl and $W^-$ is a chlorine, bromine, iodine, p-tosylate or lower alkyl sulfate anion.

4. The diquaternized compound of claim 1 which is N,N,N'-trimethyl-N'-octadecyl bis(pyrrolidonylmethyl)-1,3-propylene diammonium chloride.

5. The diquaternized compound of claim 1 which is N,N,N'-trimethyl-N'-dodecyl-bis(pyrrolidonylmethyl)-1,2-ethylene diammonium chloride.

6. The diquaternized compound of claim 1 which is N,N,N'-trimethyl-N'-nonyl bis(pyrrolidonylmethyl)-1,2-ethylene diammonium chloride.

* * * * *